United States Patent [19]

Tritsch

[11] Patent Number: 4,552,560

[45] Date of Patent: Nov. 12, 1985

[54] RESEALABLE ADHESIVE TAB FASTENER

[75] Inventor: Ludwig Tritsch, Wilmette, Ill.

[73] Assignee: Personal Products Company, Milltown, N.J.

[21] Appl. No.: 566,751

[22] Filed: Dec. 21, 1983

Related U.S. Application Data

[63] Continuation-in-part of Ser. No. 236,406, Feb. 23, 1981, abandoned.

[51] Int. Cl.$^4$ .................... A41B 13/02; A61F 13/16
[52] U.S. Cl. ................................................ 604/390
[58] Field of Search ....................................... 604/390

[56] References Cited

U.S. PATENT DOCUMENTS

| | | | |
|---|---|---|---|
| 3,848,596 | 11/1974 | Pennau | 604/390 |
| 3,951,149 | 4/1976 | Ness et al. | 604/390 |
| 4,020,842 | 3/1977 | Richman et al. | 604/390 |
| 4,043,340 | 8/1977 | Cepuritis | 604/390 |
| 4,044,767 | 8/1977 | Tritsch | 604/390 |
| 4,049,001 | 9/1977 | Tritsch | 604/390 |
| 4,186,744 | 2/1980 | Ness | 604/390 |

*Primary Examiner*—Arthur P. Demers
*Attorney, Agent, or Firm*—Martha A. Michaels

[57] ABSTRACT

An adhesive resealable tab fastener means suitable for use on a disposable diaper is provided which minimizes tearing of the tab fastener means itself or tearing it from the diaper when opening and closing repeatedly. The tab fastener means is provided with a grippable holding means and a grippable carrying tape segment. By being able to grip both parts of the tab fastener means, accidental tearing or rupturing of the fastener or diaper is minimized.

5 Claims, 9 Drawing Figures

RESEALABLE ADHESIVE TAB FASTENER

BACKGROUND OF THE INVENTION

This application is a continuation-in-part of copending application Ser. No. 236,406 filed Feb. 23, 1981 now abandoned.

This invention relates to a resealable adhesive tab fastener means suitable for use on a disposable diaper.

Disposable diapers provide substantial advantages and convenience over diapers intended to be laundered and reused, particularly when they are used away from home. In recent years many different disposable diapers have been proposed and some have been successful in the marketplace. A typical disposable diaper structure comprises a moisture-retaining absorbent batt of high liquid holding capacity enclosed between a moisture-permeable soft facing sheet and a moisture-impervious backing sheet, generally made of a plastic film. Typical disposable diaper structures are shown in U.S. Pat. No. 3,612,055 to Mesek et al and 3,938,522 to Repke.

As may be seen from the above cited patents, it is desirable to obviate the problems that are inherent in closure systems which utilize extraneous fasteners such as safety pins, snaps and zippers. To this end, adhesive closures have presented acceptable solutions which eliminate the need for pins.

Although tape tab fastening means have become a suitable substitute for extraneous fasteners such as pins, a suitable tape tab fastening system needs to simulate the ability of an extraneous fastener to be opened and, subsequently, closed. Some rather successful attempts have been made to provide resealable adhesive tape tab fasteners. However, most prior tape tab systems have not provided this flexibility. The commercially available tape tabs which are used on disposable diapers generally cannot be opened readily to check for soiling or for repositioning the diaper. On most, if not all occasions, undesirable rupture of the outside sheet of the diaper occurs when the tape tab itself is torn in order to check inside the diaper. This tearing has made refastening unmanageable or impossible and frequently results in the loss of a possibly unsoiled diaper.

In an attempt to solve the foregoing problems, U.S. Pat. No. 3,848,596 to Pennau teaches a tape tab fastener fastening means which allows an originally fastened diaper to be opened and subsequently closed. The tape tab consists of two adhesive areas on each tab covered by two release sheets. On the first closure, only one release sheet is removed to expose pressure-sensitive adhesive. Upon adjustment or inspection, the tape is peeled from the fastened position or the tab torn and the other release sheet is removed exposing fresh adhesive for a subsequent fastening. This arrangement is practical for only two fastenings, the original and one more, and has a serious drawback that undesirable rupture of the diaper can occur when peeling off the tape tab if the diaper user does not choose to tear the tab itself. With a torn fastening area, refastening is very difficult even with a freshly exposed adhesive area on the tape.

Several other U.S. Pat. Nos. such as 3,616,114, 3,951,149, 4,049,001 and 4,186,744 have provided resealable tape closures. Whereas these patents provide systems which may have some degree of success, in each case the user faces the problem of potential tear on the diaper or the manufacturer faces the problem of having to use more than one kind of adhesive in the tape tab system. The present invention provides a resealable adhesive tab fastener means requiring only one kind of adhesive and which does not tear away from the diaper upon opening and closing.

SUMMARY OF THE INVENTION

According to the present invention, an improved economical resealable adhesive tab fastener means is provided for use in disposable diapers. This tab fastener means does not require use of more than one type of adhesive nor does the tab fastener tear the diaper when reopened. Consequently, the tab fastener means of the present invention is used for the original closure and subsequent closings around the infant to provide a good strong adhesive attachment of the diaper.

The resealable adhesive tab fastener means of the present invention comprises a carrying tape segment which has an innerface and an outerface and includes a fixed end secured to the diaper and a free end. The free end includes a gripping means at the terminating end of the free end portion. Also provided is a transferable holding means which is adhesively, but releasably, carried on the innerface of the free end of the carrying tape segment. The holding means is a tape segment having an adhesive-coated face on the face opposite the face adhesively, but releasably, attached to the carrying tape segment. The holding means is at least coextensive with the free end of the carrying tape segment and has a gripping means at the terminating end nearest the gripping means of the carrying tape segment. Thus, in use of the resealable tab fastener means of the present invention, each of the tape segments are gripped, the lower one being held as the holding means while the upper one is pulled from the lower tape segment. Both sections of the tab fastener means are held in the hands preventing tearing of the tab fastener means itself and tearing away from the diaper surface. An adhesive with sufficient strength to prevent accidental opening of the diaper can be used, because the user has complete control of the tab fastener when reopening by use of both gripping means. The provision of two gripping means allows opening of the fastener without application of pressure to the body of the wearer of the diaper.

The improved resealable tab fastener means of the present invention allows one to inspect or adjust the diaper during the service of the diaper. Whereas many disposable diapers have to be discarded even when unsoiled because of torn tabs or rupture of the diaper, the improved system of the present invention provides the economical advantage of inspections and reuse of the diaper until soiled. Upon refastening, the tape tabs provide a good strong securement to the diaper. Further features are the economy of manufacture and the assurance that neither the tape tab nor the diaper will tear upon multiple closings.

DETAILED DESCRIPTION OF THE PRESENT INVENTION

Figure 1:
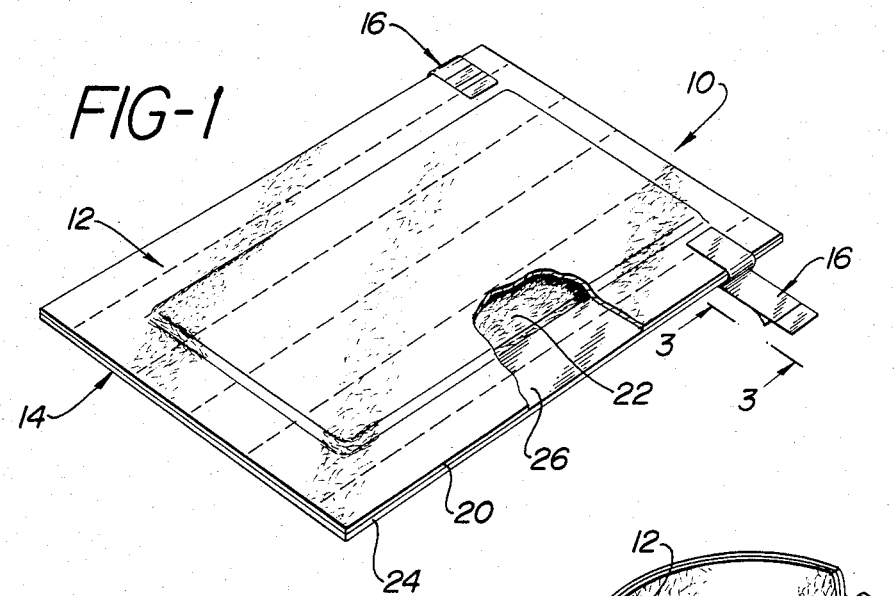
FIG. 1 is a perspective view partially broken away to show the interior detail of an open, unfolded diaper in accordance with the present invention.

Referring to FIG. 1, a typical diaper 10 comprises a moisture-pervious facing sheet 20 defining a diaper inside surface 12 and overlying moisture-retaining absorbent pad 22. The backing sheet 24 is made of a moisture-impervious material and defines a diaper outside surface 14. The absorbent pad 22 is somewhat smaller than the backing sheet 24 and is centrally disposed thereon, however, the absorbent pad 22 can be made co-extensive with the backing sheet 24 if desired. The facing sheet 20 is substantially co-extensive with the backing sheet 24. Both the facing sheet 20 and the pad 22 can be anchored to the backing sheet 24 by means of adhesive beads 26, glue spots, or in any other convenient manner. For example, if the backing sheet 24 is made of a thermoplastic material, the facing sheet 20 and the pad 22 can be attached thereto by heat bonding. The resealable tab fastener means 16 are shown in FIG. 1 in a closed storage position and in an open position ready for use.

Figure 2:
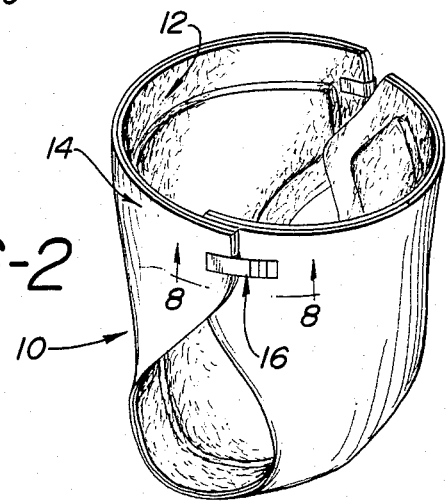
FIG. 2 is a perspective view of the diaper of FIG. 1 in a configuration assumed by the diaper when placed about the wearer.

FIG. 2 shows the diaper of FIG. 1 in a closed position using the tab fastener means 16 to secure the diaper 10 about the wearer. The facing surface 12 is shown on the interior and the backing sheet 24 provides the exterior cover 14.

Figure 3:
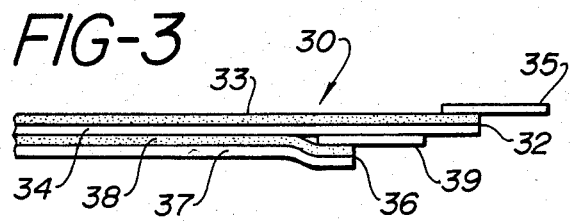
FIG. 3 is an enlarged, fragmentary cross-sectional view of the tape tab of the diaper of FIG. 1 taken along line 3—3.

FIG. 3 depicts a fragmentary cross-sectional view of a tab fastener means 30 which view is provided along lines 3—3 of FIG. 1. The carrying tape segment 36 consists of an adhesive layer 38, a release surface 37, and a gripping means 39. The transferable holding means 32 consists of an adhesive layer 33, an exterior surface which is non-adhesive 34, and a gripping means 35. The adhesive layer 33 is first fastened to the exterior diaper surface when first closing the diaper. For opening and then resealing, the adhesive surface 38 is released from the release surface 34 by utilization of the gripping means 35 in one hand and the gripping means 39 in the other hand and pulling in opposite directions. This use is further illustrated in FIGS. 8 and 8A. The gripping means depicted in FIG. 3 is a fingerlift gripping means which consists of a non-adhesive piece fastened at the terminating end of the tape segment.

Figure 4:
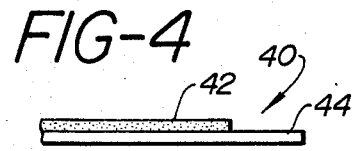
FIG. 4 is a cross-sectional view of a gripping means of a tab fastener means of the present invention.

FIG. 4 depicts another type of gripping means 40 wherein the terminating end of the tape segment 44 is not coated with adhesive 42.

Figure 5:
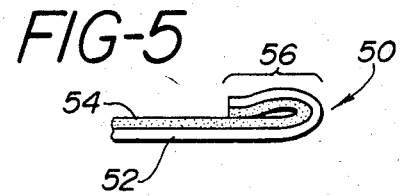
FIG. 5 is a cross-sectional view of still another gripping means of a tab fastener means of the present invention.

FIG. 5 illustrates still another gripping means 50 whereupon the adhesive layer 54 is turned back on itself to provide the end 56 whereupon only the non-adhesive surface 52 is exposed.

Figure 6:
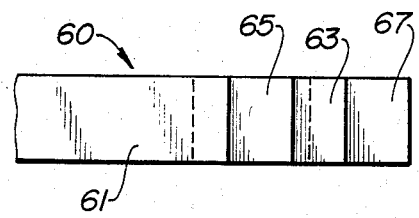
FIG. 6 is a fragmentary plan view of a tab fastener means of the present invention.

FIG. 6 illustrates a plan view of a resealable tab fastener means 60 whereupon the non-adhesive surface 61 analagous to the non-adhesive surface 37 of FIG. 3 is shown. The gripping means 65 is provided for the tape segment 61 which comprises the carrying tape segment of the tab fastener means of the present invention. The tape segment 63 depicts the transferable holding means having a gripping means 67.

Figure 7:
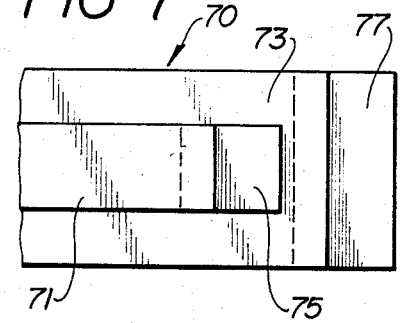
FIG. 7 is a fragmentary plan view of still another tab fastener means of the present invention.

FIG. 7 depicts another tab fastener means 70 of the present invention. In this instance, the holding means tape segment 73 is larger in area than the carrying tape segment 71. The gripping means 77 for the holding means tape segment 73 is of commensurate size. Also, the gripping means 75 for tape segment 71 is commensurate in size. The larger holding means provides an expanded landing area for closing the tab fastener after opening.

Figure 8:
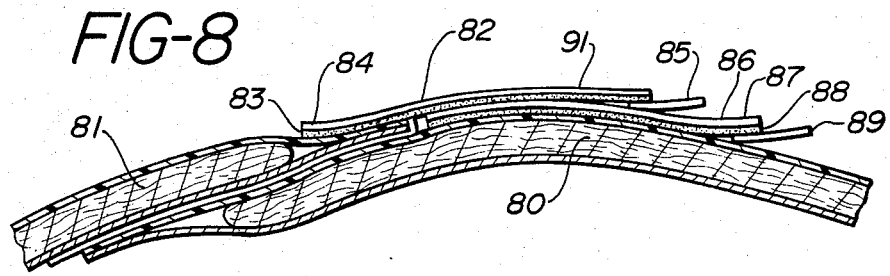
FIG. 8 is a fragmentary cross-sectional view of a tab fastener means taken along line 8—8 of FIG. 2.
Figure 8A:
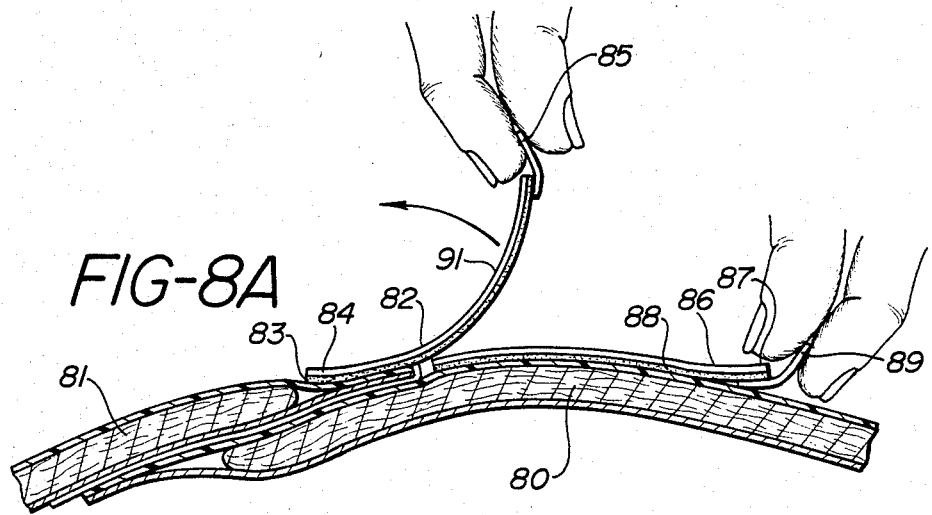
FIG. 8A is a fragmentary cross-sectional view of the tab fastener of FIG. 8 in an opened position.

FIG. 8 depicts a fragmentary view of the tab fastener means 16 of FIG. 2 along lines 8—8. The front surface of the diaper 80 is held securely to the back portion of the diaper 81 by a combination of the fixed end adhesive 83 of the carrying tape segment 82 and the transferable holding means adhesive layer 88. When reopening the diaper, the carrying tape segment working end 91 is pulled away from the holding means 86 by gripping the carrying tape segment gripping means 85 in one hand and the holding means gripping means 89 in the other hand and pulling the adhesive mass 83 away from the release surface 87. The diaper then opens, retaining the carrying tape segment 82 on the back portion of the diaper and the holding means segment 86 on the front portion 80 of the diaper. In order to reseal the diaper the carrying tape segment working end 91 is replaced against the holding means 86 and the adhesive layer 83 readheres to the release surface 87. The opening and closing steps may be repeated as often as desired.

The resealable tab fastener means of the present invention may be adhered to the diaper surface in any manner desired. The tab fastener means should be firmly affixed to the diaper surface so that upon use of the resealable features of the present invention, the tab does not become dislodged.

When the diaper is in a stored state prior to its use, the adhesive surface of the holding means should be protected in such a way as not to accidentally adhere to the surface of the diaper prematurely. This can be accomplished by use of a removable release strip, or a release strip which remains attached to a portion of the tab fastener, or a release surface which is adhered to the diaper surface in a position to permit storage of the tab fastener in a closed but releasable state.

Adhesive tabs suitable for the purpose of the present invention can be made from a wide variety of backing materials provided that such materials are sufficiently flexible. Preferred materials for this purpose are polyalkylene webs such as polyethylene or polypropylene paper, fabric and the like. Particularly preferred are webs which are oriented along the narrow dimension of the tab or webs which have filament reinforcements therein.

The pressure-sensitive layers such as adhesive coatings 83 and 88 in FIG. 8, are provided by applying a coating of a pressure-sensitive adhesive composition known in the art to be the appropriate surfaces of the tape segments 82 and 86, respectively. The applied adhesive should have good tack, good cohesive strength, good resistance to moisture and good resistance to aging. Illustrative of such adhesive compositions are mixtures of natural or synthetic rubber, zinc oxide and various resins, also lactices of natural or synthetic rubber or water dispersions of acrylate tacky polymers or co-polymers, or adhesive compounds based on ethylene vinyl acetate polymers, or block co-polymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber, U.S. Pat. No. 2,880,862 to Sermattei, and U.S. Pat. No. 2,985,554 to Dickard.

Referring again to FIG. 1, several different types of facing materials may be used for the diaper facing sheet 20. For example, a facing sheet may be made up of a mixture of fibers consisting predominantly of inexpensive short cellulosic fibers such as wood pulp fibers or cotton linters in amounts of 75–98%, the balance being textile length fibers, such as rayon, as described in U.S. Pat. No. 3,663,348 to Liloia et al.

Generally the facing sheet material suitable for use in the invention will have fabric weights in the range of about 0.5 to about 5 oz./yd.$^2$ and densities of less than 0.15 gms./cc. The dry strength of the facing sheet for a fabric typically having a weight of about 1.5 oz./yd.$^2$ is generally at least 0.15 lbs. per inch of width in the machine direction and at least 0.1 lbs. per inch of width in the cross direction. Such fabrics have unusually good elongation, loft, softness and drape characteristics.

A fabric sheet may also be made of an apertured non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked and may be arranged into various patterns as is well known to those skilled in the art. A suitable binder may be utilized to help retain the fibers in their rearranged locations as is also well known by those skilled in the art. The fabric can be made of naturally occurring fibers, synthetic fibers, or blends thereof. Typical facing sheets may be made of a polyester-type material and may have a weight of about 0.7 oz./yd.$^2$.

In addition, the facing sheet can be formed of a non-apertured material such as a non-woven isotropic web or the like. In all of the aforementioned facing materials, the material should be relatively hydrophobic so as to retard wicking within the facing layer. Also suitable are porous polymeric sheet materials, such as polyalkylene webs having a fibrous surface and the like.

The highly moisture absorbent fibrous pad or batt 22 which usually is substantially rectangular in shape but smaller than the facing sheet and the backing sheet can be formed in accordance with the teachings of U.S. Pat. No. 3,612,055 to Mesek et al. If desired, a highly moisture absorbent layer can be provided substantially coextensive with the backing sheet and the facing sheet.

A suitable backing sheet material for the diapers disclosed in the present application can be an opaque polyethylene web. Another suitable material for this purpose is a polyethylene terephthalate web. Typical disposable diapers which can be fitted with tape tab adhesive fasteners described here and above are shown in U.S. Pat. No. 3,612,055 to Mesek et al and U.S. Pat. No. 3,683,916 to Mesek et al. Other suitable disposable diaper structures which can be improved by the improved tape tab fasteners are shown in U.S. Pat. No. Reissue 26,151 to Duncan et al.

In use, a diaper equipped with the adhesive fasteners of the present invention is applied to the infant by laying out the diaper on a suitable flat surface and placing the infant thereon so that the waist underlying end of the diaper is that having the tab fastener means. The other end of the diaper then extends downwardly between the infant's legs. Next the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corner so that the diaper snuggly encircles the infant's waist and provides a custom fit. The adhesive fasteners are then prepared for use by exposing the adhesive surface and applying the free-working end of the holding means. The tabs are then used to secure the diaper in the desired position by simply urging the pressure-sensitive adhesive surface in contact with the adjacent outer surface of the diaper and can be detached and refastened as described above. The applied diaper assumes a configuration illustrated in FIG. 2.

Fifty mothers of toddlers were supplied with a popular commercial diaper having conventional tape tab fasteners and with a less popular diaper having tape tab fasteners of the present invention: the mothers were regular users of the popular commercial diaper. The less popular diaper experienced an overall win of 28 to 21 with one mother reporting no preference. When the mothers were questioned about the tab fasteners specifically, 46 said they would buy a diaper with the tab fastener of the present invention. The tab fastener of the present invention was overwhelmingly preferred by mothers used to a conventional tape tab fastener.

The foregoing description and the drawings are illustrative but are not to be taken as limiting. Still other variations and modifications are possible without departing from the spirit and scope of the present invention.

I claim:

1. A resealable adhesive tab fastener means suitable for use on a disposable diaper comprising:
    (a) a carrying tape segment having an innerface and an outerface and including a fixed end secured to the diaper and a free end which includes a gripping means at the terminating end of the free end portion; and
    (b) a transferable holding means adhesively, but releasably, carried on the innerface of the free end of said carrying tape segment, said holding means being a tape segment having an adhesive coated face on the face opposite the face adhesively, but releasably attached to said carrying tape segment, said holding means being at least co-extensive with the free end of said carrying tape segment and having a gripping means at the terminating end nearest the gripping means of said carrying tape segment said gripping means being provided by the absence of adhesive on the tape segment at the terminating end thereof, a fingerlift comprising a separate piece of material secured to the adhesive surface, or an adhesive-to-adhesive turned over portion of the tape segment at the terminating end thereof, said gripping means allowing the opening of said fastener without application of pressure to the body of the wearer of said diaper.

2. The tab fastener means of claim 1 wherein the holding means is sufficient in length to substantially cover the free end of the carrying tape segment.

3. The tab fastener means of claim 2 wherein the holding means is sufficient in length to extend beyond the gripping means of the carrying tape segment.

4. The tab fastener means of claim 1 wherein the holding means is larger in area than the free end of the carrying tape segment.

5. A disposable diaper having a facing sheet defining a diaper inside surface for direction toward an infant, a moisture-impervious backing sheet substantially co-extensive with said facing sheet and defining a diaper outside surface, an absorbent panel positioned between said facing sheet and said backing sheet and a resealable adhesive tab fastener means which comprises:

(a) a carrying tape segment having an innerface and an outerface and including a fixed end secured to the diaper and a free end which includes a gripping means at the terminating end of the free end portion; and (b) a transferable holding means adhesively, but releasably, carried on the innerface of the free end of said carrying tape segment, said holding means being a tape segment having an adhesive coated face on the face opposite the face adhesively, but releasably attached to said carrying tape segment, said holding means being at least co-extensive with the free end of said carrying tape segment and having a gripping means at the terminating end nearest the gripping means of said carrying tape segment said gripping means being provided by the absence of adhesive on the tape segment at the terminating end thereof, a fingerlift comprising a separate piece of material secured to the adhesive surface, or an adhesive-to-adhesive turned over portion of the tape segment at the terminating end thereof, said gripping means allowing the opening of said fastener without application of pressure to the body of the wearer of said diaper.

* * * * *